US012642433B2

(12) United States Patent
Ferris et al.

(10) Patent No.: US 12,642,433 B2
(45) Date of Patent: Jun. 2, 2026

(54) QUANTITATIVE MEASUREMENT OF THE PERIVASCULAR SPACE FOR CNS AND BRAIN DISORDERS

(71) Applicant: Northeastern University, Boston, MA (US)

(72) Inventors: Craig Ferris, Holden, MA (US); Ju Qiao, Boston, MA (US); Praveen Kulkarni, East Walpole, MA (US); Codi Gharagouzloo, Medford, MA (US)

(73) Assignee: Northeastern University, Boston, MA (US)

( * ) Notice: Subject to any disclaimer, the term of this patent is extended or adjusted under 35 U.S.C. 154(b) by 582 days.

(21) Appl. No.: 17/425,123

(22) PCT Filed: Jan. 27, 2020

(86) PCT No.: PCT/US2020/015223
§ 371 (c)(1),
(2) Date: Jul. 22, 2021

(87) PCT Pub. No.: WO2020/154732
PCT Pub. Date: Jul. 30, 2020

(65) Prior Publication Data
US 2022/0110524 A1 Apr. 14, 2022

Related U.S. Application Data

(60) Provisional application No. 62/796,925, filed on Jan. 25, 2019.

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *A61K 49/06* (2013.01); *G01R 33/5601* (2013.01); *G01R 33/5617* (2013.01)

(58) Field of Classification Search
CPC ...... A61B 5/0042; A61B 5/055; A61K 49/06; G01R 33/5601; G01R 33/5617
See application file for complete search history.

(56) References Cited

U.S. PATENT DOCUMENTS 7,788,722 B1 8/2010 Njemanze et al.
7,962,960 B2 6/2011 Fudge
(Continued)

FOREIGN PATENT DOCUMENTS

CN 102548571 A 7/2012
RU 2315559 C1 1/2008
(Continued)

OTHER PUBLICATIONS

Bilston et al., "Arterial Pulsation-driven Cerebrospinal Fluid Flow in the Perivascular Space: A Computational Model," Computer Methods in Biomechanics and Biomedical Engineering, 6(4): 235-241 (2003).

(Continued)

*Primary Examiner* — Rochelle D Turchen
(74) *Attorney, Agent, or Firm* — Foley Hoag LLP; Dana M. Gordon; A. Wzorek

(57) ABSTRACT

Disclosed are methods for quantification of a perivascular space in a subject's central nervous system. The methods include administering contrast agent into cerebrospinal fluid of the subject; performing quantitative ultra-short time-to-echo contrast-enhanced magnetic resonance imaging (QUTE-CE MRI) on a region of interest of the subject's brain; and determining presence of the contrast agent in the perivascular space within the region of interest.

32 Claims, 7 Drawing Sheets

(51) Int. Cl.
| | |
|---|---|
| *A61K 49/06* | (2006.01) |
| *G01R 33/56* | (2006.01) |
| *G01R 33/561* | (2006.01) |

(56) References Cited

U.S. PATENT DOCUMENTS

| | | | |
|---|---|---|---|
| 8,201,257 | B1 | 6/2012 | Andres et al. |
| 9,274,193 | B2 | 3/2016 | Johnson |
| 10,338,180 | B2 | 7/2019 | McMillan et al. |
| 2001/0031242 | A1 | 10/2001 | Cremillieux et al. |
| 2002/0147803 | A1 | 10/2002 | Dodd et al. |
| 2005/0215881 | A1 | 9/2005 | Van Zijl et al. |
| 2007/0080685 | A1 | 4/2007 | Bydder et al. |
| 2009/0246145 | A1 | 10/2009 | Small |
| 2009/0264733 | A1 | 10/2009 | Corum et al. |
| 2010/0129292 | A1 | 5/2010 | Jerosch-Herold et al. |
| 2012/0092010 | A1 | 4/2012 | Corum et al. |
| 2012/0150048 | A1 | 6/2012 | Kang et al. |
| 2012/0179028 | A1 | 7/2012 | Caravan et al. |
| 2012/0268122 | A1 | 10/2012 | Carl |
| 2012/0289511 | A1 | 11/2012 | Alam |
| 2014/0084919 | A1 | 3/2014 | Johnson |
| 2015/0065865 | A1 | 3/2015 | Leigh et al. |
| 2016/0000945 | A1 | 1/2016 | Nedergaard et al. |
| 2017/0079581 | A1 | 3/2017 | Walczak et al. |
| 2017/0102439 | A1 | 4/2017 | McMillan et al. |
| 2019/0180139 | A1 | 6/2019 | Zach et al. |
| 2019/0246938 | A1 | 8/2019 | Gharagouzloo et al. |
| 2019/0247662 | A1 | 8/2019 | Poltroak |
| 2020/0051246 | A1 | 2/2020 | Carmi |
| 2021/0298662 | A1 | 9/2021 | Gharagouzloo et al. |
| 2022/0087562 | A1 | 3/2022 | Ferris et al. |

FOREIGN PATENT DOCUMENTS

| | | | |
|---|---|---|---|
| WO | WO-2017/019182 | A1 | 2/2017 |
| WO | WO-2018/094076 | A1 | 5/2018 |
| WO | WO-2020/023980 | A1 | 1/2020 |
| WO | WO-2020/142696 | A1 | 7/2020 |
| WO | WO-2020/154732 | A1 | 7/2020 |

OTHER PUBLICATIONS

International Search Report and Written Opinion for International Application No. PCT/US2020/015223 dated Apr. 6, 2020.

Lam et al., "The ultrastructure of spinal cord perivascular spaces: Implications for the circulation of cerebrospinal fluid," Scientific Reports, 7: 12924 (2017).

Lliff et al., "A Paravascular Pathway Facilitates CSF Flow Through the Brain Parenchyma and the Clearance of Interstitial Solutes, Including Amyloid β," Sci Transl Med., 4(147): 147ra111 (2012).

Rennels et al., "Evidence for a 'Paravascular' Fluid Circulation in the Mammalian Central Nervous System, Provided by the Rapid Distribution of Tracer Protein Throughout the Brain from the Subarachnoid Space," Brain Research, 326: 47-63 (1985).

Taoka et al., "Gadolinium-based Contrast Media, Cerebrospinal Fluid and the Glymphatic System: Possible Mechanisms for the Deposition of Gadolinium in the Brain," Magnetic Resonance in Medical Sciences, 17(2):111-119 (2018).

Feraheme (ferumoxytol) injection label, from https://www.accessdata.fda.gov/drugsatfda_docs/label/2009/022180lb1.pdf) (2017).

International Search Report and Written Opinion for International Application No. PCT/US2020/012191 mailed Mar. 19, 2020.

Morrison et al., "Early Detection of Cerebral Microbleeds Following Mild Traumatic Brain Injury Using QUTE-CE MRI," Presented Nov. 7, 2018 at the Society for Neuroscience Meeting, San Diego, CA.

Arai et al., "Brain angiogenesis in developmental and pathological processes: neurovascular injury and angiogenic recovery after stroke", Febs J. vol. 276, No. 17, pp. 4644-4652, (2009).

Assini et al., "Object location memory in mice: Pharmacological validation and further evidence of hippocampal CA1 participation", Behav Brain Res. vol. 204, No. 1, pp. 206-211, (2009).

Bane, et al., "Leakage and Water Exchange Characterization of Gadofosveset in the Myocardium", Magnetic Resonance Imaging, vol. 32, No. 3, pp. 224-235, Apr. 2014.

Banerjee et al., "Novel imaging techniques in cerebral small vessel diseases and vascular cognitive impairment", Biochim. Biophys. Acta—Mot Basis Dis. 1862, pp. 926-938, (2015).

Barbier et al., "Methodology of Brain Perfusion Imaging", Journal of Magnetic Resonance Imaging, vol. 13, pp. 496-520, (2001).

Barker et al., "Relative Frequencies of Alzheimer Disease, Lewy Body, Vascular and Frontotemporal Dementia, and Hippocampal Sclerosis in the State of Florida Brain Bank", Alzheimer Dis Assoc Disord., vol. 16, No. 4, pp. 203-212, (2002).

Bremerich et al., "MR angiography with blood pool contrast agents", Eur Radial. vol. 17, No. 12, pp. 3017-3024, (2007).

Brookheimer et al., "Patterns of brain activation in people at risk for Alzheimer's disease", N Engl J Med., vol. 343, No. 7, pp. 450-456, (2000).

Brunser et al., "Accuracy of diffusion-weighted imaging in the diagnosis of stroke in patients with suspected cerebral infarct", Stroke, pp. 1169-1171, (2013).

Charidimou et al., "Sporadic cerebral amyloid angiopathy revisited: Recent insights into pathophysiology and clinica spectrum", J Neural Neurosurg Psychiatry., vol. 83, No. 2, pp. 124-137, (2012).

Chen et al., "Neurovascular abnormalities in brain disorders: highlights with angiogenesis and magnetic resonance imaging studies", J. Biomed Sci., vol. 20, pp. 1-8, (2013).

Christen et al., "High-resolution cerebral blood volume imaging in humans using the blood pool contrast agent ferumoxytol", Magn Reson Med., vol. 70, No. 3, pp. 705-710, Sep. 2013.

Cunningham et al., "Positive contrast magnetic resonance imaging of cells labeled with magnetic nanoparticles", Magn Reson Med., vol. 53, No. 5, pp. 999-1005, May 2005.

Desai et al., "Evidence of angiogenic vessels in Alzheimer's disease", J Neural Transm., vol. 116, pp. 587-597, May 2009.

Du et al., Qualitative and quantitative ultrashort-TE MRI of cortical bone, NMR Biomed., vol. 26, No. 5, pp. 489-506, May 2013.

Filippini et al., "Distinct patterns of brain activity in young carriers of the APOE-?4 allele", Proc Natl Acad Sci., vol. 106, No. 17, pp. 7209-7214, (2009).

Forshult, "Magnetic Resonance Imaging MRI—An Overview", Karlstad, Sweden: Karlstad University (2007), p. 9.

Gharagouzloo et al, "Central Nervous System Diagnostics with QUTE-CE", Poster presented at Northeastern's University ITNANO Presentation, 1 page (2014).

Gharagouzloo et al, "Contrast Enhanced Quantitative UTE(QUTE-CE) MRI for Cerebral Blood Imaging and Cancer Diagnostics", Poster presented at Northeastern University Research, Innovation and Scholarship Expo, 1 page (2014).

Gharagouzloo et al, "Diagnosing Neuropathy Early with QUTE-CE MRI", Poster presented at IGERT Illanomedicine 1st Annual Nanomedicine Day, 1 page (2015).

Gharagouzloo et al, "ISMRM Abstract", ISMRM Abstract submitted and poster presented at ISMRM, 1 page (2014).

Gharagouzloo et al, "Longitudinal Monitoring of Nanoparticle Accumulation in PC-3 Tumors", Poster presented at Northeastern University Research, Innovation and Scholarship Expo, 1 page (2015).

Gharagouzloo et al, "Positive Contrast Ultrashort TE imaging with Ferumoxytol Contrast Agent". Poster presented at NCIGT Workshop, 2012, 1 page.

Gharagouzloo et al, "Quantitative Imaging of Magnetic Nanoparticles in Mouse Vasculature", Poster presented at IGERT Nanomedicine 1st Annual Nanomedicine Day, 1 page (2015).

Gharagouzloo et al, "Quantitative Positive Contrast MRI with Iron Oxide Nanoparticles". Poster presented at Northeastern University ITNANO Presentation, 1 page (2013).

Gharagouzloo et al, "Quantitative ultra-high resolution MR imaging using magnetic nanoparticles", Poster presented at NCIGT Workshop, 1 page (2014).

(56) References Cited

OTHER PUBLICATIONS

Gharagouzloo et al, "Ultra-short TE imaging with SPIONs—Bright prospects for in vivo applications.", Abstract presented at Northeastern University Research, Innovation and Scholarship Expo, 1 page (2013).

Gharagouzloo et al, "UTE Angiography with ferumoxytol", Abstract Published at IEEE NEBEC, retrieved from eeexplore.ieee.org/document/6972796; 2 pages (2014).

Gharagouzloo et al., "Environment and mobility influence on magnetic nanoparticles with Ferumoxytol", Poster ; presented at World Molecular Imaging Congress, 1 page (2012).

Gharagouzloo et al., "Functional neuroimaging using dynamic radial 3D UTE pulse sequences", Poster presented at ISMRM, 1 page (2017).

Gharagouzloo et al., "Quantitative In Vivo Concentration Determination of Magnetic Nanoplatforms with Ultra-Short TE Magnetic Resonance Imaging UTE", Poster presented at First International Translational Nanomedicine Conference, Boston, MA,, 1 page (2013).

Gharagouzloo et al., "Quantitative vascular measurements in ApoE-E :-4 knock-in female rats before onset of AD", International Society for Magnetic Resonance in Medicine, ISMRM, 2030 Addison Street, 7th Floor, Berkeley, CA 94704 USA, No., Jun. 1, 2018, XP040701222, 3 pages (2014).

Gharagouzloo et al., "Quantitative vascular neuroimaging of the rat brain using superparamagnetic nanoparticles: New insights on vascular organization and brain function", Neuroimage.; 163:24-33. doi: 10.1016/j.neuroimage. 21 pages (2017).

Gharagouzloo et al., Contrast Enhanced Quantitative UTE (QUTE-CE) MRI for Cerebral Blood Imaging and Cancer Diagnostics, Rise 2014, Abstract ID# 301, Northeastern University, Apr. 10, 2014.

Gharagouzloo, C.A. et al, "Quantitative Contrast-Enhanced MRI with Superparamagnetic Nanoparticles Using Ultrashort Time-to-Echo Pulse Sequences", Magnetic Resonance Imaging, vol. 74, No. 2, 431-441; EPub; Aug. 28 (online) DOI: 10.1002/mrm.25426 (2015).

Gorelick et al., Vascular contributions to cognitive impairment and dementia: A statement for healthcare professionals from the American Heart Association/American Stroke Association, Stroke, vol. 42, No. 9, pp. 2672-2713, (2011).

Greenberg et al., "Cerebral microbleeds: a guide to detection and interpretation", Lancet Neural., 19 pages (2009).

Guo et al., "The Vasculome of the Mouse Brain", PLoS One. vol. 7, 17 pages (2012).

Gupta et al., "Impaired AB clearance: A potential link between atherosclerosis and Alzheimer's disease", Front Aging Neurosci., 8 pages (2015).

Hachinski, V., "Dementia: Paradigm shifting into high gear", Alzheimers Dement., vol. 15, No. 7, pp. 985-994, Jul. 2019.

Iadecola, "The Pathobiology of Vascular Dementia", Neuron., vol. 80, No. 4, pp. 844-866, (2013).

Jack et al., "Serial PIB and MRI in normal, mild cognitive impairment and Alzheimers disease: Implications for sequence of pathological events in Alzheimers disease", Brain, vol. 132, No. 5, pp. 1355-1365, (2009).

Johnson et al., "Hybrid Radial-Cones Trajectory for Accelerated Magnetic Resonance Imaging", Magn Reson Med., vol. 77, No. 3, pp. 1068-1081, Mar. 2017.

Kim et al., In Vivo Quantification of Transvascular Water Exchange During the Acute Phase of Permanent Stroke, Magn Reson Med., vol. 60, No. 4, pp. 813-821, Oct. 2008.

Kim, S. et al., "Cerebral Blood Volume MRI with Intravascular Superparamagentic Iron Oxide Nanoparticles", NMR Biomedicine, vol. 26, No. 8, pp. 949-962, Aug. 2012.

Kwon et al., "Simultaneous evaluation of vascular morphology, blood volume and transvascular permeability using SPION-based, dual-contrast MRI: imaging optimization and feasibility test", NMR In Biomedicine, vol. 28, pp. 624-632, (2015).

Kwong et al., "Dynamic magnetic resonance imaging of human brain activity during primary sensory stimulation", Proc Natl Acad Sci USA, vol. 89, No. 12, pp. 5675-5679, (1992).

Leaston et al., "Neurovascular imaging with QUTE-CE MRI in APOE4 rats reveals early vascular abnormalities", Plos One Aug. 27, 16 pages (2021).

Li et al., "Angiogenesis and improved cerebral blood flow in the ischemic boundary area detected by MRI after administration of sildenafil to rats with embolic stroke", Brain Res., vol. 1132, No. 1, pp. 185-192, (2007).

Mandeville, "Iron fMRI measurements of CBV and implications for BOLD signal", Neuroimage, vol. 62, No. 2, pp. 1000-1008, (2012).

Marques et al., "Low-Field MRI: An MR Physics Perspective," Journal of Magnetic Resonance Imaging, vol. 49, No. 6, pp. 1528-1549, (2019).

Murase, "Generalized equation for describing the magnetization in spoiled gradient-echo imaging", Magnetic Resonance Imaging, vol. 29, No. 5, pp. 723-730, Jun. 2011.

Reijmer et al., "Ischemic brain injury in cerebral amyloid angiopathy", J Cereb Blood Flow Metab, 15 pages (2016).

Reiman et al., "Brain imaging and fluid biomarker analysis in young adults at genetic risk for autosomal dominant Alzheimer's disease in the presenilin 1 E280A kindred: A case-control study", Lancet Neurol., vol. 11, No. 12, pp. 1048-1056, (2012).

Rohrer et al., "Comparison of Magnetic Properties of MRI Contrast Media Solutions at Different Magnetic Field Strengths, Investigative Radiology", vol. 40, No. 11, pp. 715-724, Nov. 2005.

Schabel et al., "Uncertainty and bias in contrast concentration measurements using spoiled gradient echo pulse sequences", Phys Med Biol., vol. 53, No. 9, pp. 2345-2373, (2008).

Schild, H.H., "MRI made easy( . . . well almost)", Berlin: Schering AG, p. 96 (1990).

Seevinck et al., "Magnetic resonance imaging of brain angiogenesis after stroke", Angiogenesis, vol. 13, No. 2, pp. 101-111, (2010).

Semple et al., "Brain development in rodents and humans: Identifying benchmarks of maturation and vulnerability to injury across species", Prog Neurobiol., vol. 106, pp. 1-16, Jul. 2013.

Shi et al., "Update on cerebral small vessel disease: a dynamic whole-brain disease", BMJ, vol. 1, No. 3, pp. 83-92, (2016).

Stuber et al., "Positive contrast visualization of iron oxide-labeled stem cells using inversion-recovery with ON-resonant water suppression (IRON)", Magn Reson Med., vol. 58, pp. 1072-1077, (2007).

Sutphin et al. "Male Pelvic MR Angiography", Magnetic Resonance Imaging Cln. N. Am. vol. 22, No. 2, May 2014.

Tropres et al., Vessel size imaging, Magn Reson Med., vol. 45, pp. 397-408, (2001).

Uh et al., "Cerebral blood volume in Alzheimer's disease and correlation with tissue structural integrity", Neurobiology of Aging, vol. 31, No. 12, pp. 2038-2046, (2010).

Walker-Samuel et al., "Reference tissue quantification of DCE-MRI data without a contrast agent calibration", Phys Med Biol., vol. 52, No., 3, pp. 589-601, Jan. 2007.

Wang et al., "Improving detection specificity of iron oxide nanoparticles (ION Ps) using the SWIFT sequence with long T2 suppression", Magn Reson Imaging, vol. 32, No. 6, pp. 671-678, Jul. 1, 2014.

Wardlaw et al., "Mechanisms underlying sporadic cerebral small vessel disease: insights from neuroimaging", Lancet Neurol., vol. 12, No. 5, pp. 1-27, (2013).

Wardlaw et al., "Neuroimaging standards for research into small vessel disease and its contribution to ageing and 11eurodegeneration", Lancet Neurol., vol. 12, No. 8, pp. 822-838, (2013).

Wey et al., "A review of current imaging methods used in stroke research", Neurol Res., vol. 35, No. 10, pp. 1092-1102, Dec. 2013.

Yankeelov et al., "Dynamic Contrast Enhanced Magnetic Resonance Imaging in Oncology: Theory, Data Acquisition, Analysis and Examples", Curr Med Imaging Rev., vol. 3, No. 2, pp. 91-107, 2009.

Zhang et al., "T1-Weighted Ultrashort Echo Time Method for Positive Contrast Imaging of Magnetic Nanoparticles and Cancer Cells Bound With the Targeted Nanoparticles", J Magn Reson Imaging, vol. 33, No. 1, pp. 194-202, Jan. 2011.

(56)　　　　　　　References Cited

OTHER PUBLICATIONS

Zlokovic, "Neurovascular pathways to neurodegeneration in Alzheimer's disease and other disorders", Nat. Rev Neurosci., vol. 12, No. 12, pp. 723-738, Dec. 2011.

Gharagouzloo et al, "Ultrashort TE imaging with SPIONs: bright prospects for in vivo applications", AACR/SNMMI State-of-the-Art Molecular Imaging in Cancer Biology and Therapy: Abstracts, Molecular Imaging in Cancer, Abstract No. 28, p. 9, 2013, total 36 pages.

Perles-Barbacaru, A.T. et al., "A new Magnetic Resonance Imaging method for mapping the cerebral blood volume fraction: the rapid steady-state T1 method," Journal of Cerebral Blood Flow & Metabolism 27 (2007): 618-631.

Shah et al., "Evaluating intensity normalization on MRIs of human brain with multiple sclerosis," Medical Image Analysis 15 (2011): 267-282.

Xu et al., "Dynamic Glucose Enhanced (DGE) M Ri for Combined Imaging of Blood-Brain Barrier Break Down and Increased Blood Volume in Brain Cancer," Magnetic Resonance in Medicine 74 (2015) :1556-1563.

Heye et al., "Tracer kinetic modelling for DCE-MRI quantification of subtle blood-brain barrier permeability." Neuroimage, 125, 446-455 (2016).

Wardlaw et al., "Changes in background blood-brain barrier integrity between lacunar and cortical ischemic stroke subtypes." Stroke, 39(4), 1327-1332 (2008).

QUANTITATIVE MEASUREMENT OF THE PERIVASCULAR SPACE FOR CNS AND BRAIN DISORDERS

RELATED APPLICATIONS

This application is a U.S. National Stage Application of International Application No. PCT/US20/15223, filed Jan. 27, 2020; which claims the benefit of priority to U.S. provisional patent application Ser. No. 62/796,925, filed Jan. 25, 2019.

BACKGROUND

Previous efforts to use magnetic resonance imaging (MRI) to produce reproducible biomarkers for mild traumatic brain injury (TBI) have proven ineffective. In almost all cases, increases in perivascular space are reported, but no reliable imaging method existed to quantify the volume spatially. An increased volume of the perivascular space is also noted for all neurodegenerative diseases, such as Alzheimer's Disease (AD) and Parkinson's Disease (PD), and is also linked to glymphatic flow and clearance of toxins indicated.

The volume of the perivascular space is a unique biomarker because it is found around arterioles and venules, but not capillaries (e.g. spinal cord (Lam et al. 2017)). A large body of evidence indicates that perivascular spaces represent the major route for fluid inflow from the subarachnoid space into the brain and spinal cord (Bilston et al. 2003; Iliff et al. 2012; Rennels et al. 1985) and are also the major pathway for solute clearance. Early electron microscopic studies described perivascular spaces in hamster and rat, however the anatomical details of their ultrastructure are not well understood.

There is a need for methods that allow quantification of the volume of perivascular space in a subject and thereby facilitate determining changes in the volume of perivascular space, which can be an indication of disease.

SUMMARY

Methods for quantification of a perivascular space in a subject's brain are disclosed. The perivascular space is dilated in subjects with traumatic brain injury, brain and CNS disorders. Quantification of a perivascular space in a subject's brain according to the methods disclosed herein can, for example, facilitate understanding, diagnosis and monitoring of the progress of traumatic brain injury, and brain and CNS disorders.

One embodiment is a method for quantification of a perivascular space in a subject's central nervous system comprising: administering contrast agent into cerebrospinal fluid of the subject; performing quantitative ultra-short time-to-echo contrast-enhanced magnetic resonance imaging (QUTE-CE MRI) on a region of interest of the subject's brain; and determining presence of the contrast agent in the perivascular space within the region of interest.

In some embodiments, the region of interest is the subject's brain, and the presence of the contrast agent (CA) is determined in perivascular spaces of the subject's brain.

In some embodiments, performing QUTE-CE MRI comprises applying a magnetic field to region of interest; applying a radio frequency pulse sequence with a selected repetition time (TR) and flip angle (FA) to excite protons in the region of interest, wherein the TR is less than about 10 ms, and the FA ranges from about 10° to about 30°; measuring a response signal during relaxation of the protons at a selected time-to-echo (TE) with magnetic field gradients activated to provide a T1-weighted signal from the region of interest, wherein the TE is an ultra-short time-to-echo (UTE) less than about 300 μs; and generating an image of the region of interest.

In some embodiments, the acquired signal is representative of a concentration of the CA in the region of interest.

In some embodiments, the methods disclosed herein further comprise setting the time to echo (TE) to less than 30 μs.

In some embodiments, the TR is set to a value below about 5 ms, the TE is set to a UTE value and the FA is selected to be around the Ernst angle of the contrast-enhanced blood.

In some embodiments, the methods disclosed herein further comprise setting the TE to zero using a Zero TE (ZTE) sequence.

In some embodiments, the methods disclosed herein further comprise setting the repetition time (TR) to a value from about 2 to about 10 ms.

In some embodiments, the methods disclosed herein further comprise setting the flip angle to a value from about 10° to about 25°.

In some embodiments, QUTE-CE MRI is performed before presence of the contrast agent in the perivascular space and is subsequently performed after contrast agent is present in the perivascular space.

In some embodiments, the contrast agent comprises ferumoxytol and QUTE-CE MRI is performed before administration of the contrast agent.

In some embodiments, the methods described herein comprise determining the presence of contrast agent in the perivascular space at a plurality of times based on respective quantitative signal intensity obtained by the QUTE-CE MRI at these times in the perivascular space.

In some embodiments, the methods described herein comprise determining the presence of contrast agent in the perivascular space when respective quantitative signal intensity obtained by QUTE-CE MRI for the perivascular space is near or at maximum value.

In further aspects of these embodiments, ferumoxytol is administered at a dose of about 2 to about 14 mgFe/kg body weight.

In further aspects of these embodiments, ferumoxytol is administered at a dose of about 3 to about 4 mgFe/kg body weight.

In further aspects of these embodiments, ferumoxytol is administered at a dose of about 7-14 mg/kg bodyweight in animals or 2-7 mg/kg bodyweight in humans.

In some embodiments, the subject is a non-human mammal.

In some embodiments, the subject is a human.

In some embodiments, the subject has traumatic brain injury (TBI), type 2 diabetes, stroke, or a CNS disorder.

In some embodiments, the subject has a CNS disorder; and the CNS disorder is amyotrophic lateral sclerosis, frontotemporal dementia, Huntington's disease, Alzheimer's disease or related dementia, or Parkinson's disease.

In some embodiments, the subject has an early stage CNS disorder selected from amyotrophic lateral sclerosis, Huntington's disease, Alzheimer's disease or related dementia, and Parkinson's disease.

In some embodiments, the subject has minor cognitive impairment.

In some embodiments, the administering of contrast agent is intrathecal.

DETAILED DESCRIPTION

Figure 1A:
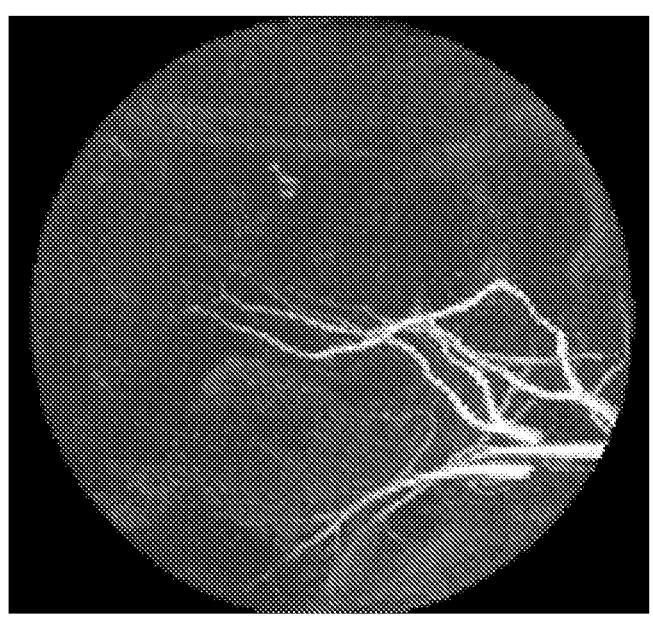
FIG. 1A shows a 3D UTE Precontrast maximum intensity projection (MIP) image.

The various concepts introduced above and discussed in greater detail below may be implemented in any of numerous ways, as the described concepts are not limited to any particular manner of implementation. Examples of specific implementations and applications are provided primarily for illustrative purposes.

Methods for quantification of the volume of perivascular spaces in a subject's CNS are disclosed. The methods are based on the introduction of contrast agent (CA) into a subject's cerebral spinal fluid and its flow into perivascular spaces. After injection of CA into the cerebrospinal fluid, the CA perfuses throughout the central nervous system (CNS) and enhances the contrast of the cerebrospinal fluid (CSF). The presence of CA in the perivascular space can be measured, for example, by using ultrashort time echo (UTE) pulse sequences, such as with the QUTE-CE method, to generate a quantitative signal intensity, which can be followed longitudinally from the time of CA injection, for example, to determine the time course of signal intensity in the perivascular space. The presence of CA in a perivascular space is determined by the kinetics of flow into and flow out of the perivascular space. It has been found that quantification of the perivascular space is most accurate when done at a time when CA has substantially filled the perivascular space but before significant flow of CA out of the perivascular space, which is associated with significant decrease in signal intensity obtained by the QUTE-CE method. Following the signal intensity spatially (e.g., on a voxel-wise basis) and longitudinally allows determination of an optimum time for quantification of the perivascular space. It has further been found that the flow of ferumoxytol into and through perivascular spaces depends on whether the subject is awake or anesthetized. Specifically, it has been found that quantification of perivascular space in awake rats typically is most accurate when done within 5 to 15 minutes of injection of ferumoxytol, and that longer times are required for anesthetized rats.

The methods described herein can be used to quantify the volume of the perivascular spaces (particularly, the brain's perivascular spaces) in a subject, but they can also more generally be used to determine the dynamics of CA perfusion throughout the CNS including into the perivascular spaces and to quantify the volume of CSF in parts other than the perivascular spaces or the volume of CSF throughout the brain or CNS (including perivascular spaces). Patterns of the ratio, or spatial volume, of intraventricular space to the gray and white matter can reflect important measures of brain or CNS disease progression.

The volume of CSF including perivascular spaces in the CNS or brain quantified with the methods described herein, can be compared to the respective volume of a control group of healthy subjects. If the quantified volume, for example, of the perivascular spaces of a given subject's brain, is significantly larger than that of the control group, this can be an indication of traumatic brain injury (including mild traumatic brain injury), a brain disorder and/or CNS disorder of the given subject. Further, quantifying the volume, for example, of the perivascular spaces of a given subject's brain over days, weeks, or years can allow following progression of a traumatic brain injury, brain disorder and/or CNS disorder, by comparing the volumes quantified at different times. For example, if the perivascular spaces are increasing over time, this can be an indication of worsening of a brain disorder or disease. Accordingly, the methods described herein can be used in methods of diagnosing or monitoring the progression of a traumatic brain injury, brain disorder or CNS disorder.

A further embodiment is a method for diagnosing or monitoring the progression of a traumatic brain injury, brain disorder or CNS disorder in a subject, comprising using any one of the methods described herein for quantifying volume of CSF in a part (e.g., in the brain's perivascular spaces) of the subject's CNS, and comparing the volume so quantified with a respective volume of one or more control subjects. In an aspect of this embodiment, the quantified volume is compared to the respective volume of the same subject measured at an earlier time, for example, at a time that the subject was healthy (i.e., did not have a disorder causing dilation of one or more perivascular spaces such as traumatic brain injury, brain or CNS disorder).

Quantitative ultra-short time-to-echo (QUTE-CE) MRI, as previously described in (Gharagouzloo et al., 2015), (Gharagouzloo et al., 2017) and (U.S. Patent Application Publication No. 2019/0246938, entitled "Quantitative Magnetic Resonance Imaging of the Vasculature"; incorporated by reference) can be used in the methods disclosed herein. QUTE-CE is a quantitative, ultrashort time to echo, contrast-enhanced magnetic resonance imaging technique. The technique can be used to accurately measure contrast agent concentration in the blood, to provide clear, high-definition angiograms, and to measure absolute quantities of cerebral blood volume on a voxel-by-voxel basis.

QUTE-CE MRI is a technique that allows producing a quantitative signal intensity for MRI. This quantitative signal intensity has been shown to be used to quantify contrast agent concentration in blood (Gharagouzloo et al., 2015) and quantify contrast-enhanced blood per voxel in the brain (Gharagouzloo et al., 2017).

In the underlying theory of QUTE-CE MRI, the intensity magnitude $I_M$ of each voxel is a function of standard MRI parameters governed by the Spoiled Gradient Echo (SPGR) equation, $$I_M = K\rho \cdot e^{(-TE/T_2)} \cdot \sin(FA) \frac{1 - e^{(-TR/T_1)}}{1 - e^{(-TR/T_1)} \cdot \cos(FA)}, \qquad (1)$$

where TE is the time-to-echo, TR is the repetition time, and FA is the flip angle. TE, TR, and FA are user-defined image acquisition parameters. $T_1$ and $T_2$ are relaxation time constants dependent on the local environment of each voxel, which is mutable via CAs, and dependent on the magnetic field strength. K is a constant determined by the properties of the receive coil and $\rho$ is the proton density of the medium. TE is typically chosen to be <100 μs to eliminate suscepti-bility-induced signal modifications. The choice of a very low TR (<5 ms) with a 3D volume excitation pulse minimizes effects from the extravascular water exchange and elimi-nates signal enhancement from blood flow within the cranial space. This can be achieved with either hard pulse or slab-select pulse. Setting the FA at the Ernst angle maxi-mizes the T1-enhanced signal and minimizes sensitivity to small perturbations in FA.

In some embodiments, performing QUTE-CE MRI com-prises applying a magnetic field to region of interest; apply-ing a radio frequency pulse sequence at a selected TR and at a magnetic field gradient to provide a selected FA to excite protons in the region of interest, wherein the TR is less than about 10 ms, and the FA ranges from about 10° to about 30°; measuring a response signal during relaxation of the protons at a selected TE to acquire a $T_1$-weighted signal from the region of interest, wherein the time to echo is an ultra-short time to echo less than about 300 μs; and generating an image of the region of interest.

In some embodiments, the acquired signal is representa-tive of a concentration of the CA in the region of interest.

In some embodiments, the disclosed methods further comprise setting the TE to less than about 30 μs.

In some embodiments, the disclosed methods further comprise setting the TR to a value from about 1 to about 10 ms.

In some embodiments, the disclosed methods further comprise setting the flip angle to a value from about 10° to about 25°.

In some embodiments, QUTE-CE MRI is performed using a TE of about 13 μs, a TR of about 4 ms and an FA of about 20° with a high radio frequency (RF) pulse band-width of 200 kHz. This results in a pulse duration of 6.4 μs which is short compared to the $T_2$ of the approximate ferumoxytol concentration (Gharagouzloo et al., 2017). Choosing a pulse duration which is short compared to the $T_2$ of the approximate ferumoxytol concentration minimizes signal blur and reduce the probability for a curved trajectory of the magnetization vector $M_z$ (Gharagouzloo et al., 2017).

QUTE-CE MRI can be performed with commercially available magnetic resonance imaging devices, as they are found, for example, in clinical, hospital and medical labo-ratory settings. QUTE-CE MRI is a technique that produces a quantitative signal intensity for MRI. This quantitative signal intensity has been shown to be used to quantify contrast agent concentration in blood (Gharagouzloo et al., 2015) and quantify contrast-enhanced blood per voxel in the brain (Gharagouzloo et al., 2017).

The methods disclosed herein, include performing the QUTE-CE MRI method on a region of interest of the subject's CNS. For example, a region of interest can be a part of the subject's brain or the entirety of the subject's brain.

After administration of CA (e.g., intrathecal administra-tion of ferumoxytol) to the subject, it takes some time for CA to flow into perivascular spaces. Accordingly, typically, a pre-contrast image of the region of interest is determined, and, subsequently, one or more images are acquired to determine a baseline (i.e., before ferumoxytol has been able to localize in the perivascular spaces, subsequently, one more images are acquired to determine ferumoxytol con-centration in the perivascular spaces of the region of interest.

In some embodiments, QUTE-CE MRI is performed before injection of CA, e.g., ferumoxytol.

Further information regarding performing the QUTE-CE MRI method, including preparing a brain atlas containing a plurality of anatomical and functional regions, obtaining a high-resolution anatomical data set of the region of interest, and image processing are provided in (Gharagouzloo et al., 2017). The methods described herein can include imaging the region of interest with voxels registered to a brain atlas.

The methods disclosed herein include administration of a CA. Suitable CA are paramagnetic and flow into the perivas-cular space. Typically, the CA is ferumoxytol. Ferumoxytol is an ultra-small superparamagnetic iron oxide nanoparticle (SPION) with a dextran coating. Since the size exceeds the cutoff (~6 nm) for glomerular filtration, ferumoxytol is not cleared by the kidney, and instead is an excellent blood pool CA with a long intravascular half-life of about 15 h (Bremer-ich et al., 2007). Ferumoxytol is approved for iron-defi-ciency anemia. Ferumoxytol has been found to be particu-larly useful as contrast agent in the methods described herein because of its localization to the perivascular space with a prolonged residence time (i.e., favorable pharmacokinetics). This facilitates longitudinal and highly accurate measure-ments.

In some embodiments, the CA is not cleared by the kidney of the subject. In other embodiments, the CA has a size which enables kidney filtration.

In the methods described herein, contrast agent is injected into the cerebrospinal fluid. Typically, the contrast agent is ferumoxytol. Commercially available Feraheme® injection can be used, which is a sterile aqueous colloidal product that is formulated with mannitol. It is a black to reddish brown liquid, and is commercially available in single-dose 17 mL vials containing 510 mg of elemental iron. Each mL of the sterile colloidal solution of Feraheme® Injection contains 30 mg of elemental iron, 30 mg polyglucose sorbitol carboxym-ethylether, and 44 mg of mannitol. The formulation is isotonic with an osmolality of 270-330 mOsm/kg. The product contains no preservatives, and has a pH of 6 to 8.

In some embodiments, ferumoxytol is administered at a dose of about 1 mgFe/kg body weight to about 8 mgFe/kg body weight, about 2 mgFe/kg body weight to about 7 mgFe/kg body weight, about 2 mgFe/kg body weight to about 6 mgFe/kg body weight, about 2 mgFe/kg body weight to about 4 mgFe/kg body weight, or about 4 mgFe/kg body weight.

As used herein, "body weight" refers to the body weight of the subject.

In some embodiments, determining presence of contrast agent (e.g., ferumoxytol) includes assigning signal intensity acquired using QUTE-CE MRI on a voxel basis to perivascular space within the region of interest. Further, determining presence of contrast agent (e.g., ferumoxytol) can include calculating the voxel wise change of the intensity of the acquired signal from a first acquired signal at a time before contrast agent is present in the one or more perivascular spaces within the region of interest (typically, at a time before administration of contrast agent) to a subsequently acquired signal after contrast agent administration. When signal is acquired repeatedly (e.g., continuously or periodically) from the time that contrast agent (e.g., ferumoxytol) is administered, the methods disclosed herein also allow following the dynamics of contrast agent perfusion in the region of interest.

The methods disclose herein can be used to quantify one or more perivascular spaces in subjects in need thereof. As used herein, a "subject in need thereof", refers to a subject who is at risk to have, is suspected to have, and/or has a traumatic brain injury, brain disorder or CNS disorder.

In embodiments, the subject in need thereof is a subject who has or had a traumatic brain injury, has had or has a stroke, has type 2 diabetes, or has a central nervous system (CNS) disorder, for example, amyotrophic lateral sclerosis, frontotemporal dementia, Huntington's disease, Alzheimer's disease or related dementia, Parkinson's disease, and mental illnesses, such as schizophrenia and depression.

In embodiments, the subject in need thereof is a subject who has an early stage CNS disorder. Examples of early stage CNS disorders include, but are not limited to, early stage amyotrophic lateral sclerosis, early stage Huntington's disease, early stage Alzheimer's disease or related dementia, early stage Parkinson's disease, early stage frontotemporal dementia, or an early stage minor cognitive impairment.

As used herein, "subject" refers to a mammal, including, but not limited to, a human or non-human mammal, such as a bovine, equine, canine, ovine, rodent, or feline.

Disease models in small animals, including transgenic models of multiple CNS disorders, such as Huntington's Disease, Alzheimer's disease and Parkinson's disease, can also be quantified with the technology.

The Alzheimer's Association study published a study on the economic benefit early AD detection. The model included the entire U.S. population in 2018, with early detection measures beginning in 2020. Differences in expected costs come from two primary sources: "1) there is a 'spike' in costs during the period immediately before and after diagnosis, and this spike is smaller when diagnosis is made during the MCI stage, and 2) medical and long-term care costs are lower in people with diagnosed and managed MCI and dementia than in people with unmanaged MCI and dementia."

With 80 M people in the age range of 45-64, a 1% diagnostic check per year from this population would yield 800 K scans, with a total gross cost of $1.6 B-$2.8 B. If all AD cases with mixed vascular pathology are diagnosed early the cost benefits for the current US population would be as much as $3.16 trillion (calculated as 40% of the potential $7.9 trillion in savings for all AD), or simply $12.72-$92.56 billion per year from 2025-2050 (see Graph); specifically, these cost savings would be to Medicare (47%), Medicaid (32%) and other insurers (20%). Based on the potential financial benefits to insurers, we project that insurance companies will cover the costs of these early diagnostic tests. With insurance companies willing to pay and 80 M people standing to benefit, we expect health facilities and MRI manufacturers to integrate and use the technology.

Further Definitions

As used herein, the singular forms "a," "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "intrathecal administration of a contrast agent" or "administering intrathecally a contrast agent" refers to a route of administration of contrast agent via an injection into the subject's spinal canal or subarachnoid space so that the contrast agent reaches the cerebrospinal fluid (CSF).

As used herein, "perivascular spaces (PVSs)" are pial-lined, fluid-filled structures found in characteristic locations throughout the brain. They are also known as Virchow-Robin spaces.

EXAMPLES

The present examples are non-limiting implementations of the present technology.

Quantitative vascular mapping of the rat brain CSF starts with acquisition of pre- and post-ferumoxytol scans. A 3D UTE sequence with optimized parameters for perivascular contrast and quantification are utilized. Field corrections for coil sensitivity (B1−) and flip-angle distribution (B1+) are applied along with motion correction between the pre- and post-contrast images. A voxel-wise calculation for the quantitative CSF (qCSF) is performed to produce the qCSF maps after using a two-volume CSF and blood/tissue model with knowledge of CSF intensity obtained from large ventricles. For the rat models described here, voxels are distributed into an anatomically segmented atlas with 173 regions for quantitative analysis of the whole brain. Statistically significant abnormalities are found by comparing healthy rats to those of the relevant disease model or indication.

METHOD/PROCEDURE: Just prior to imaging, rats were anesthetized with 2-3% isoflurane. The scalp was incised and a burr hole made in the skull for implantation of sterile PE10 tubing (Braintree Scientific) aimed at the right lateral cerebroventricle using the stereotaxic coordinates: 1.0 mm posterior to the bregma, 2.0 mm lateral to the midline, and 4.0 mm in depth from dura. The tubing, ca 60 cm in length and prefilled with Ferumoxytol, was fixed in place with cyanoacrylic cement and connected to a 0.3 mL syringe needle filled with the contrast agent Ferumoxytol that could be positioned just outside the bore of the magnet. Ferumoxytol concentration for the second animal was 10 mg/ml Fe. Volume injected for each animal is 20 microliters. An anatomy imaging and a UTE imaging were taken before contrast administration. Time series of UTE imagings were taken immediately after ferumoxytol injection.

Scan parameters: TE/TR=0.01 ms/4 ms, FA=20 degrees, 3 cm isotropic field of view (FoV) with 166.7 micrometer isotropic resolution, scan time 7 minutes.

Figure 1B:
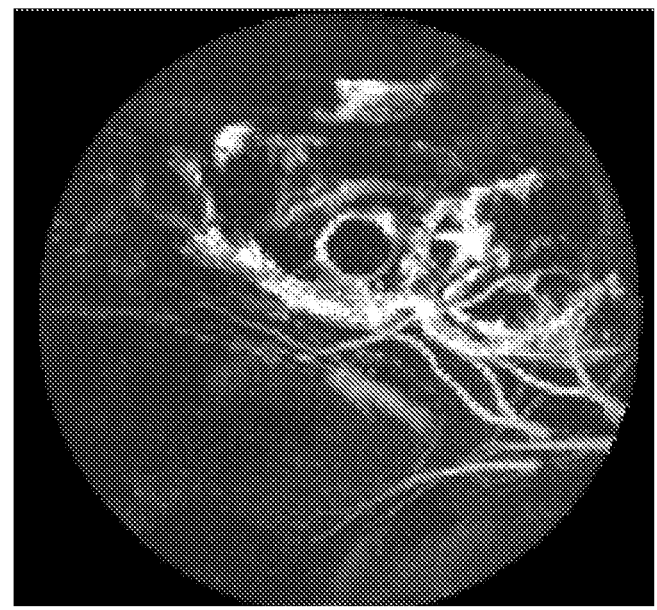
FIG. 1B shows a 3D UTE postcontrast at 56 minutes postcontrast MIP image.

FIGS. 1A and 1B show (i) 3D UTE Precontrast maximum intensity projection (MIP) image, and (ii) 3D UTE postcontrast at 56 minutes postcontrast MIP image, respectively.

Figure 2A:
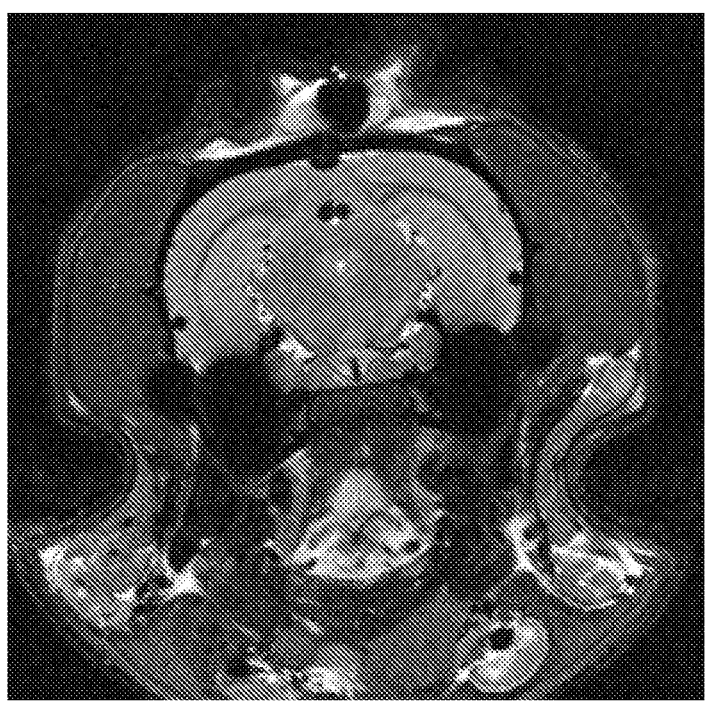
FIG. 2A shows 2D axial image slices of T1-weighted anatomy.
Figure 2B:
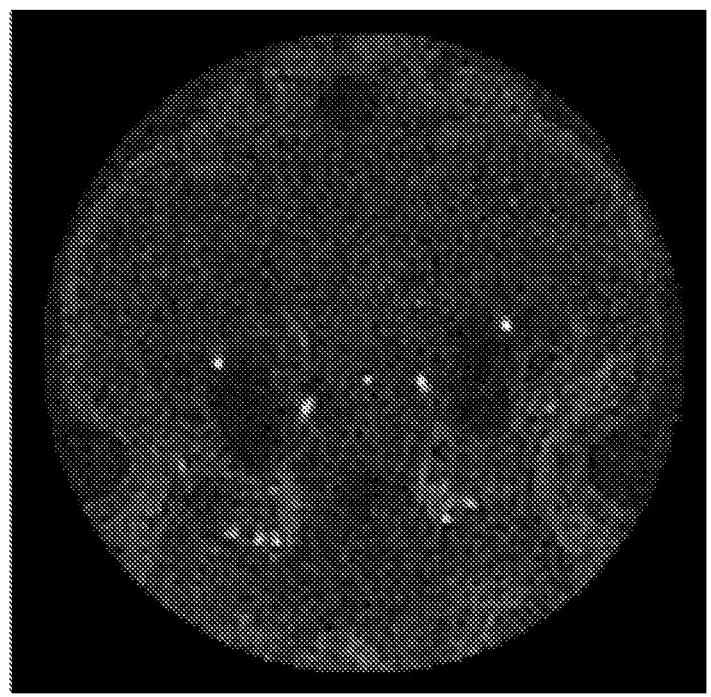
FIG. 2B shows 2D axial image slices of 3D UTE Precontrast.
Figure 2C:
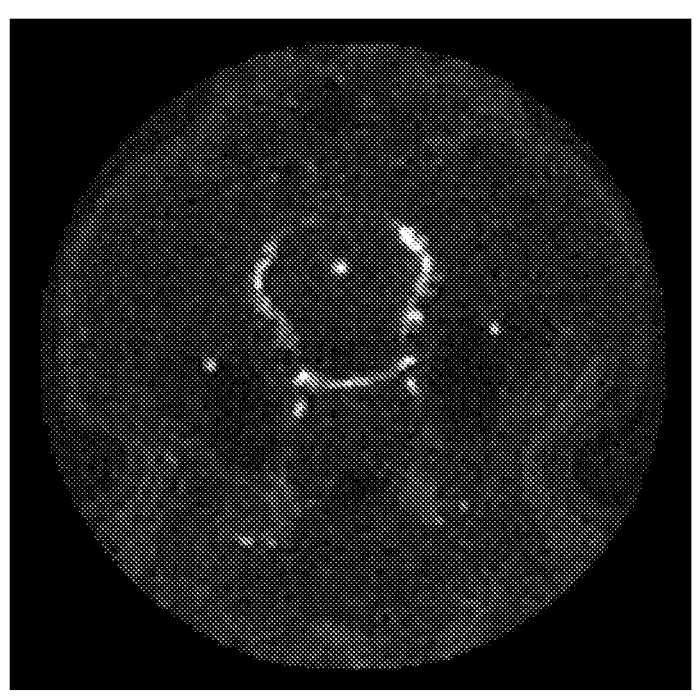
FIG. 2C shows 2D axial image slices of 3D UTE postcontrast at 56 minutes postcontrast.
Figure 3A:
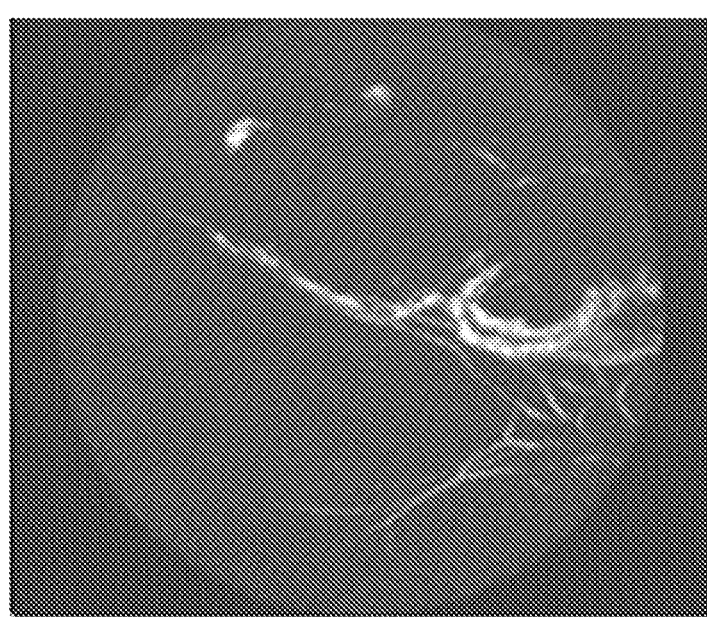
FIG. 3A shows a maximum intensity projection image after 7 minutes.
Figure 3B:
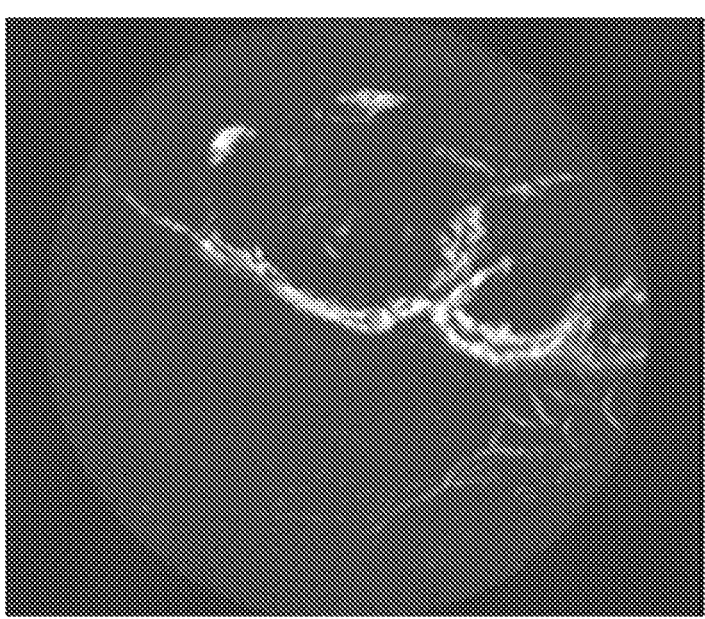
FIG. 3B shows a maximum intensity projection image after 14 minutes.
Figure 3C:
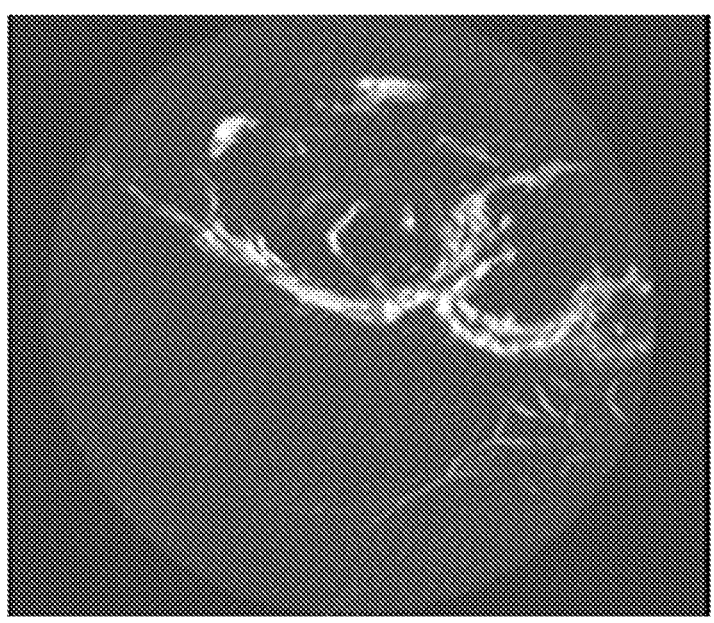
FIG. 3C shows a maximum intensity projection image after 21 minutes.
Figure 3D:
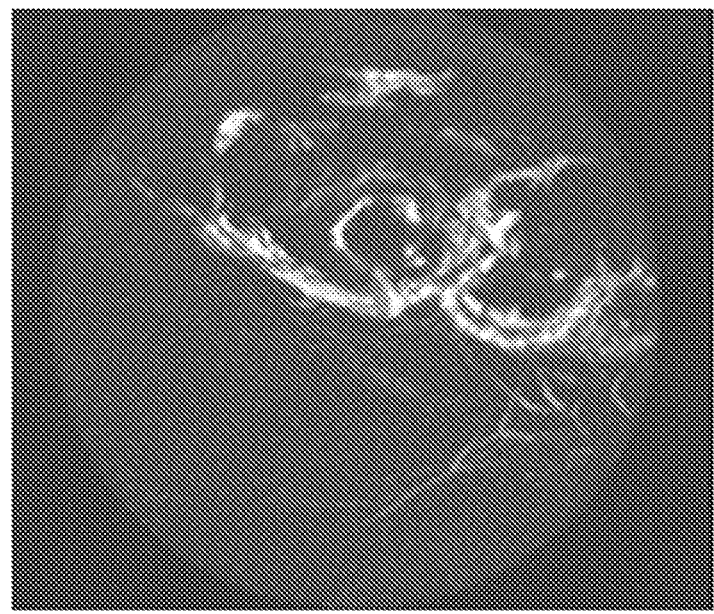
FIG. 3D shows a maximum intensity projection image after 28 minutes.
Figure 3E:
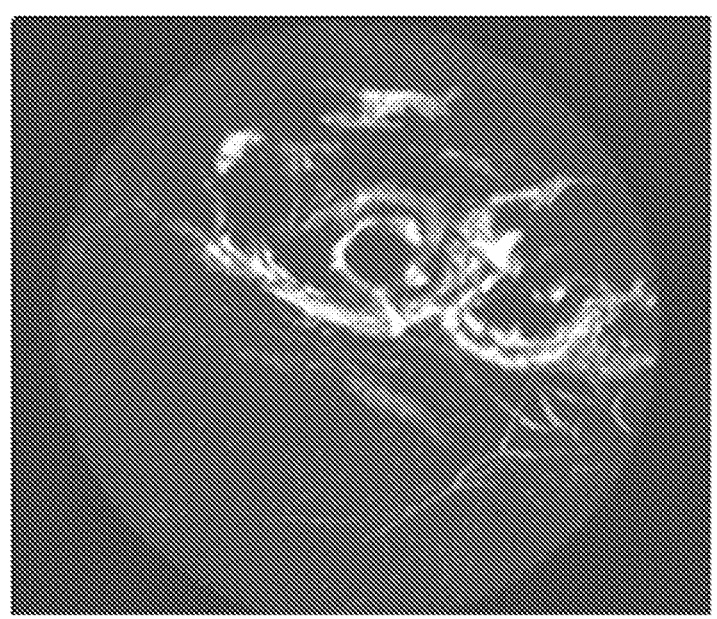
FIG. 3E shows a maximum intensity projection image after 35 minutes.
Figure 3F:
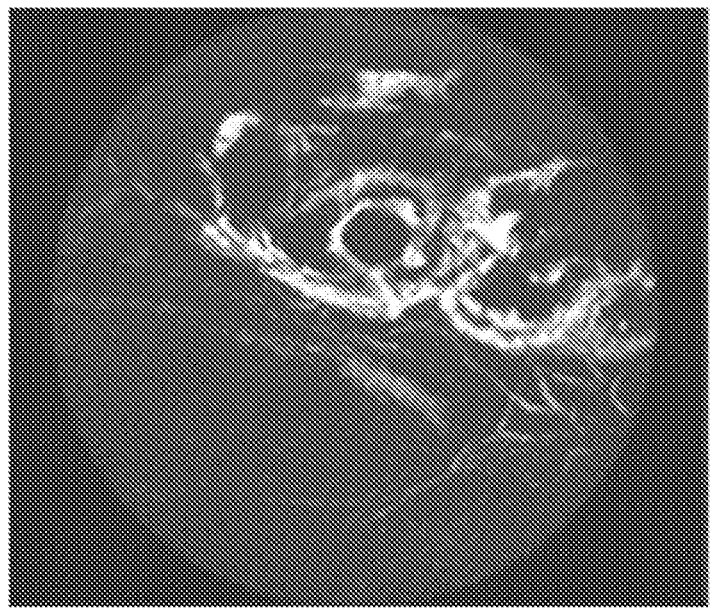
FIG. 3F shows a maximum intensity projection image after 42 minutes.
Figure 3G:
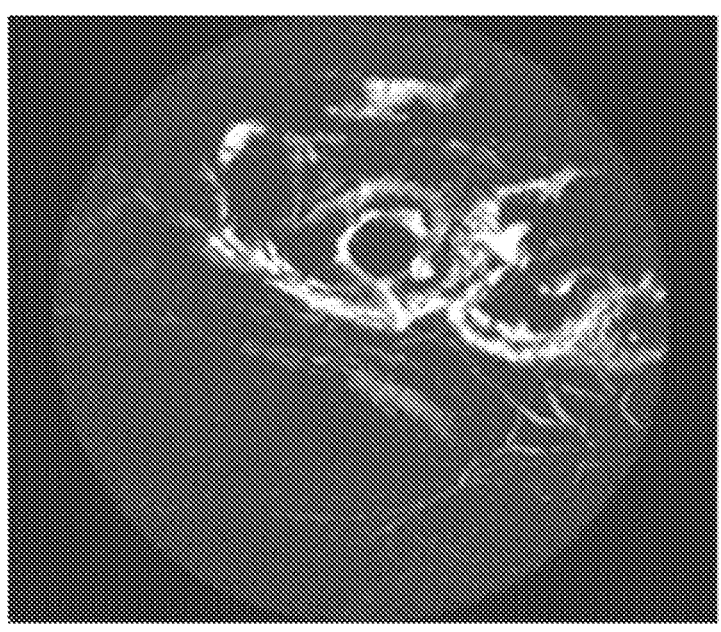
FIG. 3G shows a maximum intensity projection image after 49 minutes.
Figure 3H:
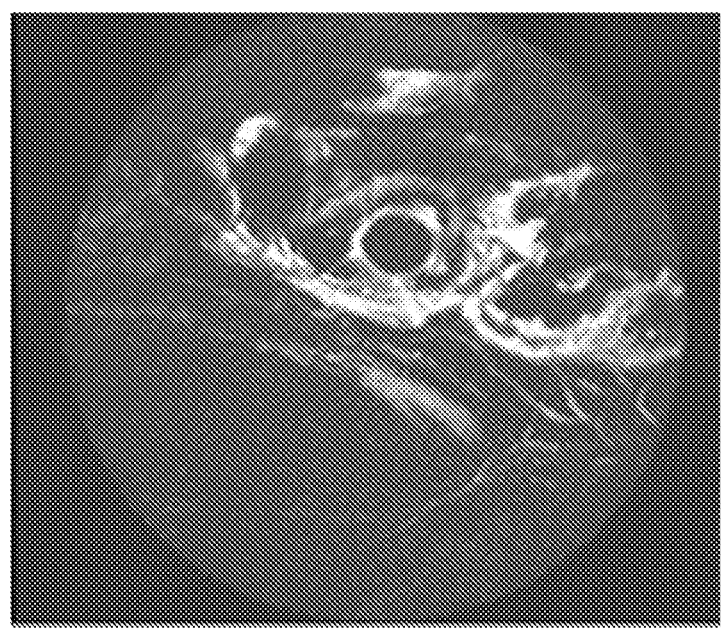
FIG. 3H shows a maximum intensity projection image after 56 minutes.

FIGS. 2A, 2B and 2C show 2D axial image slices of (i) T1-weighted anatomy, (ii) 3D UTE Precontrast, and (iii) 3D UTE postcontrast at 56 minutes postcontrast, respectively.

FIGS. 3A, 3B, 3C, 3D, 3E, 3F, 3G, and 3H show Maximum intensity projection images (MIPS) of the rat demonstrating time-course of glymphatic mixing using the method. All images are rendered by subtracting the first image without contrast, such that the time-course is clearly visualized. Images were run continuously with images ending after (a) 7 minutes, (b) 14 minutes, (c) 21 minutes, (d) 28 minutes, (e) 35 minutes, (f) 42 minutes, (g) 49 minutes, and (h) 56 minutes, respectively.

REFERENCES CITED

Bilston, L. E., Fletcher, D. F., Brodbelt, A. R. & Stoodley, M. A. Arterial pulsation-driven cerebrospinal fluid flow in the perivascular space: A computational model. Comput. Methods Biomech. Biomed. Engin. (2003). doi:10.1080/10255840310001606116.

Bremerich J, Bilecen D, Reimer P. MR angiography with blood pool contrast agents. European radiology 2007; 17(12): 3017-24.

Gharagouzloo C A, McMahon P N, Sridhar S. Quantitative contrast-enhanced MRI with superparamagnetic nanoparticles using ultrashort time-to-echo pulse sequences. Magn Reson Med 2015; 74(2): 431-41.

Gharagouzloo C A, Timms L, Qiao J, Fang Z, Nneji J, Pandya A, et al. Quantitative vascular neuroimaging of the rat brain using superparamagnetic nanoparticles: New insights on vascular organization and brain function. NeuroImage 2017; 163: 24-33.

Iliff, J. J. et al. A paravascular pathway facilitates CSF flow through the brain parenchyma and the clearance of interstitial solutes, including amyloid beta. Sci. Transl. Med. (2012), 4(147), 1547ra111. doi:10.1126/scitranslmed.3003748.

Lam, M. A. et al. The ultrastructure of spinal cord perivascular spaces: Implications for the circulation of cerebrospinal fluid. Sci. Rep. (2017). doi:10.1038/s41598-017-13455-4.

Rennels, M. L., Gregory, T. F., Blaumanis, O. R., Fujimoto, K. & Grady, P. A. Evidence for a 'Paravascular' fluid circulation in the mammalian central nervous system, provided by the rapid distribution of tracer protein throughout the brain from the subarachnoid space. Brain Res., 1985, 326(1), pp. 47-63.

U.S. Patent Application Publication No. 2019/0246938, entitled "Quantitative Magnetic Resonance Imaging of the Vasculature"; incorporated by reference.

The teachings of the documents cited herein are hereby incorporated by reference.

EQUIVALENTS

The present technology (including present methods) is not limited to the particular embodiments described in this application, which are intended as individual illustrations of aspects of the present technology. Many modifications and variations of the present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, compounds, compositions, disease pathologies, or devices, which can, of course, vary. It is also to be understood that the terminology used herein is for the purpose of describing particular embodiments only, and is not intended to be limiting.

What is claimed is:

1. A method for evaluation of a perivascular space in a subject, the method comprising:

determining at least one kinetic value of flow of perivascular space in a region of interest, the determining comprising:

analyzing magnetic resonance imaging (MRI) data of the region of interest, the MRI data of the region of interest comprising first MRI data captured at a first time point and second MRI data captured at a second time point, one or more of the first time point or the second time point being after (a) a paramagnetic or superparamagnetic blood pool contrast agent was introduced into cerebrospinal fluid of the region of interest of the subject and (b) an occurrence of at least partial mixing of the cerebrospinal fluid with interstitial fluid, the analyzing the MRI data comprising identifying a first signal intensity for the first time point and a second signal intensity for the second time point, wherein each of the first signal intensity and the second signal intensity is obtained via an MRI device configured with a repetition time (TR) less than 10 ms and a time to echo (TE) less than 300 μs;

calculating a longitudinal rate of a change in signal intensity in the region of interest, the longitudinal rate of change in signal intensity comprising a difference in signal intensity obtained from the paramagnetic or superparamagnetic blood pool contrast agent in at least a perivascular space of the region of interest based on a spatial volume of each of the first signal intensity and the second signal intensity; and evaluating the longitudinal rate of change in signal intensity to determine the at least one kinetic value of flow of the perivascular space within the region of interest.

2. The method of claim 1, wherein the region of interest is at least a portion of the subject's brain and the spatial volume is a volume of perivascular spaces of the at least the portion of the subject's brain.

3. The method of claim 1, wherein each of the first signal intensity and the second signal intensity is obtained at least in part by:

applying a magnetic field to the region of interest;

applying a radio frequency pulse sequence with a selected repetition time (TR) and a selected flip angle (FA) to excite protons in the region of interest, wherein the repetition time is less than about 10 ms, and the flip angle ranges from about 10° to about 30°;

measuring a response signal during relaxation of the protons at a selected time to echo (TE) with magnetic field gradients activated to provide a $T_1$-weighted signal from the region of interest, wherein the time-to-echo is an ultra-short time-to-echo, or Zero TE (ZTE), less than about 300 μs; and generating an image of the region of interest.

4. The method of claim 3, wherein each of the first signal intensity and the second signal intensity is representative of a concentration of the paramagnetic or superparamagnetic blood pool contrast agent in the region of interest.

5. The method of claim 3, further comprising setting the time to echo (TE) to less than about 30 μs.

6. The method of claim 3, further comprising setting the repetition time to a value from about 2 to about 10 ms.

7. The method of claim 3, further comprising setting the flip angle to a value from about 10° to about 25°.

8. The method of claim 1, wherein the MRI data is captured by performing quantitative ultra-short time-to-echo contrast-enhanced magnetic resonance imaging (QUTE-CE MRI), and wherein OUTE-CE MTI is performed before presence of the paramagnetic or superparamagnetic blood pool contrast agent in the perivascular space and is subsequently performed after the paramagnetic or superparamagnetic blood pool contrast agent is present in the perivascular space.

9. The method of claim 8, wherein the paramagnetic or superparamagnetic blood pool contrast agent comprises ferumoxytol and QUTE-CE MRI is performed before administration of the ferumoxytol.

10. The method of claim 8, comprising determining the presence of contrast agent in the perivascular space at a plurality of times based on respective quantitative signal intensity obtained by the QUTE-CE MRI at said times in the perivascular space.

11. The method of claim 8, wherein determining the at least one kinetic value of flow comprises determining a spatial volume of the perivascular space when respective quantitative signal intensity obtained by QUTE-CE MRI for the perivascular space is near or at maximum value.

12. The method of claim 1, wherein the contrast agent is ferumoxytol.

13. The method of claim 12, wherein ferumoxytol is administered at a dose of about 2 to about 14 mgFe/kg body weight.

14. The method of claim 1, wherein administering of the paramagnetic or superparamagnetic blood pool contrast agent is intrathecal.

15. A computing system comprising:

one or more processors; and storage encoded with instructions that, when executed by the one or more processors, cause the one or more processors to perform a method comprising:

determining at least one kinetic value of flow of tissue adjacent to vascular tissue in a region of interest of a subject, the determining comprising:

analyzing magnetic resonance imaging (MRI) data of the region of interest, the MRI data of the region of interest comprising first MRI data captured at a first time point and second MRI data captured at a second time point, one or more of the first time point or the second time point being after (a) a paramagnetic or superparamagnetic blood pool contrast agent was introduced into cerebrospinal fluid of the region of interest of the subject and (b) an occurrence of at least partial mixing of the cerebrospinal fluid with interstitial fluid, the analyzing the MRI data comprising identifying a first signal intensity for the first time point and a second signal intensity for the second time point, wherein each of the first signal intensity and the second signal intensity is obtained via an MRI device configured with a repetition time (TR) less than 10 ms and a time to echo (TE) less than 300 μs;

calculating a longitudinal rate of a change in signal intensity in the region of interest, the longitudinal rate of change in signal intensity comprising a difference in signal intensity obtained from the paramagnetic or superparamagnetic blood pool contrast agent in at least the tissue adjacent to the vascular tissue of the region of interest based on a spatial volume of each of the first signal intensity and the second signal intensity; and evaluating the longitudinal rate of change in signal intensity to determine the at least one kinetic value of flow of the tissue adjacent to the vascular tissue within the region of interest.

16. At least one non-transitory computer-readable storage medium having encoded thereon instructions that, when executed by at least one processor, cause the at least one processor to carry out a method comprising:

determining at least one kinetic value of flow of perivascular space in a region of interest of a subject, the determining comprising:

analyzing magnetic resonance imaging (MRI) data of the region of interest, the MRI data of the region of interest comprising first MRI data captured at a first time point and second MRI data captured at a second time point, one or more of the first time point or the second time point being after (a) a paramagnetic or superparamagnetic blood pool contrast agent was introduced into cerebrospinal fluid of the region of interest of the subject and (b) an occurrence of at least partial mixing of the cerebrospinal fluid with interstitial fluid, the analyzing the MRI data comprising identifying a first signal intensity for the first time point and a second signal intensity for the second time point, wherein each of the first signal intensity and the second signal intensity is obtained via an MRI device configured with a repetition time (TR) less than 10 ms and a time to echo (TE) less than 300 μs;

calculating a longitudinal rate of a change in signal intensity in the region of interest, the longitudinal rate of change in signal intensity comprising a difference in signal intensity obtained from the paramagnetic or superparamagnetic blood pool contrast agent in at least a perivascular space of the region of interest based on a spatial volume of each of the first signal intensity and the second signal intensity; and evaluating the longitudinal rate of change in signal intensity to determine the at least one kinetic value of flow of the perivascular space within the region of interest.

17. The method of claim 1, wherein evaluating the change in signal intensity is based on a time-course of the at least partial mixing of the cerebrospinal fluid with the interstitial fluid.

18. The method of claim 1, wherein the at least one kinetic value of flow comprises a rate of mixing of the paramagnetic or superparamagnetic blood pool contrast agent in the perivascular space within the region of interest.

19. The method of claim 18, wherein the evaluating further comprises, once a mixing of the paramagnetic or superparamagnetic blood pool contrast agent has reached steady state, quantifying a volume of the perivascular space within the region of interest.

20. The method of claim 19, wherein the evaluating further comprises, once the mixing of the paramagnetic or superparamagnetic blood pool contrast agent has reached steady state, determining a clearance of the paramagnetic or superparamagnetic blood pool contrast agent from the cerebrospinal fluid into a soft palate of the subject.

21. The method of claim 1, wherein the at least one kinetic value of flow of the perivascular space within the region of interest comprises a difference in an amount of the paramagnetic or superparamagnetic blood pool contrast agent in each of the perivascular space within the region of interest and a soft palate of the subject at a predetermined time point during a time-course of glymphatic mixing.

22. The method of claim 1, wherein determining the at least one kinetic value of flow of the perivascular space within the region of interest comprises determining the at least one kinetic value of flow into or out of the perivascular space within the region of interest.

23. The computing system of claim 15, wherein the at least one kinetic value of flow comprises a rate of mixing of the paramagnetic or superparamagnetic blood pool contrast agent in the tissue adjacent to vascular tissue within the region of interest.

24. The computing system of claim 23, wherein the evaluating further comprises, once a mixing of the paramagnetic or superparamagnetic blood pool contrast agent has reached steady state, quantifying a volume of the tissue adjacent to vascular tissue within the region of interest.

25. The computing system of claim 24, wherein the evaluating further comprises, once the mixing of the paramagnetic or superparamagnetic blood pool contrast agent has reached steady state, determining a clearance of the paramagnetic or superparamagnetic blood pool contrast agent from the cerebrospinal fluid into a soft palate of the subject.

26. The computing system of claim 15, wherein the at least one kinetic value of flow of the tissue adjacent to vascular tissue within the region of interest comprises a difference in an amount of the paramagnetic or superparamagnetic blood pool contrast agent in each of the tissue adjacent to vascular tissue within the region of interest and a soft palate of the subject at a predetermined time point during a time-course of glymphatic mixing.

27. The computing system of claim 15, wherein determining the at least one kinetic value of flow of the tissue adjacent to vascular tissue within the region of interest comprises determining the at least one kinetic value of flow into or out of the tissue adjacent to vascular tissue within the region of interest.

28. The computer-readable storage medium of claim 16, wherein the at least one kinetic value of flow comprises a rate of mixing of the paramagnetic or superparamagnetic blood pool contrast agent in the perivascular space within the region of interest.

29. The computer-readable storage medium of claim 28, wherein the evaluating further comprises, once a mixing of the paramagnetic or superparamagnetic blood pool contrast agent has reached steady state, quantifying a volume of the perivascular space within the region of interest.

30. The computer-readable storage medium of claim 29, wherein the evaluating further comprises, once the mixing of the paramagnetic or superparamagnetic blood pool contrast agent has reached steady state, determining a clearance of the paramagnetic or superparamagnetic blood pool contrast agent from the cerebrospinal fluid into a soft palate of the subject.

31. The computer-readable storage medium of claim 16, wherein the at least one kinetic value of flow of the perivascular space within the region of interest comprises a difference in an amount of the paramagnetic or superparamagnetic blood pool contrast agent in each of the perivascular space within the region of interest and a soft palate of the subject at a predetermined time point during a time-course of glymphatic mixing.

32. The computer-readable storage medium of claim 16, wherein determining the at least one kinetic value of flow of the perivascular space within the region of interest comprises determining the at least one kinetic value of flow into or out of the perivascular space within the region of interest.

* * * * *